(12) United States Patent
Kraemer et al.

(10) Patent No.: US 6,875,438 B2
(45) Date of Patent: Apr. 5, 2005

(54) PREPARATIONS FOR TOPICAL ADMINISTRATION OF SUBSTANCES HAVING ANTIANDROGENIC ACTIVITY

(75) Inventors: Karl Theodor Kraemer, Langen (DE); Karl-Heinz Nietsch, Neuss (DE); Rainer Pooth, Dreieich-Gotzenhain (DE); Uwe Muenster, Berlin (DE); Wolfgang Mehnert, Berlin (DE); Monika Schaefer-Korting, Berlin (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/422,280

(22) Filed: Apr. 24, 2003

(65) Prior Publication Data

US 2003/0229129 A1 Dec. 11, 2003

Related U.S. Application Data

(60) Provisional application No. 60/407,521, filed on Aug. 29, 2002.

(30) Foreign Application Priority Data

Apr. 27, 2002 (DE) .......................................... 102 18 963

(51) Int. Cl.$^7$ .................... A61K 9/127; A61K 31/4166; C07D 233/78
(52) U.S. Cl. ..................... 424/401; 514/391; 548/319.5
(58) Field of Search ...................... 548/319.5; 514/391; 424/401

(56) References Cited

U.S. PATENT DOCUMENTS

| | | | |
|---|---|---|---|
| 5,411,981 A | 5/1995 | Gaillard-Kelly | |
| 5,627,201 A | 5/1997 | Gaillard-Kelly et al. | |
| 5,750,553 A | * 5/1998 | Claussner et al. | 514/392 |
| RE35,956 E | 11/1998 | Gaillard-Kelly et al. | |
| 6,162,444 A | 12/2000 | Dubois | |
| 6,242,611 B1 | * 6/2001 | Claussner et al. | 548/320.1 |

FOREIGN PATENT DOCUMENTS

AU 726572 11/2000

OTHER PUBLICATIONS

List Heinz–Joachim et al., Comparison Of Chromatin Remodeling And Transcriptional Activation Of The Mouse Mammary Tumor Virus Promoter By The Androgen And Glucocorticoid Receptor, Experimental Cell Research, 250, (1999), pp. 414–422.

McClellan Karen J. et al., Finasteride A Review Of Its Use In Male Pattern Hair Loss, Drugs, 57, (1999), pp. 111–126.

Van Neste D. et al., Finasteride Increases Anagen Hair In Men With Androgenetic Alopecia, British Journal Of Dermatology, 143, (2000), pp. 804–810.

\* cited by examiner

*Primary Examiner*—Laura L. Stockton
(74) *Attorney, Agent, or Firm*—Ronald G. Ort

(57) ABSTRACT

A preparation comprising at least one form of lipid nanoparticles or a nanoemulsion comprising at least one compound of the formula I

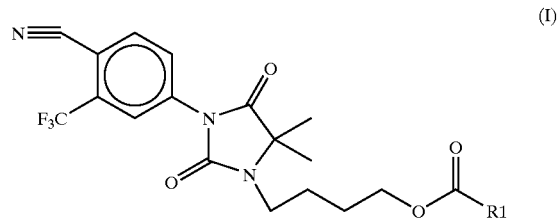

(I)

and/or one stereoisomeric form of the compound of the formula I and/or one physiologically tolerated salt of the compound of the formula I, in which R1 is —($C_5$–$C_{17}$)-alkyl or —($C_5$–$C_{17}$)-alkenyl, is suitable for the treatment of androgenic alopecia, of hirsutism, that is to say to prevent unwanted hair growth, and for the treatment of seborrhea and acne and can furthermore be employed in cosmetics.

12 Claims, No Drawings

PREPARATIONS FOR TOPICAL ADMINISTRATION OF SUBSTANCES HAVING ANTIANDROGENIC ACTIVITY

This application claims the benefit of U.S. Provisional Application No. 60/407,521, filed Aug. 29, 2002, and incorporated herein by reference.

Androgenic alopecia is the commonest form of hair loss, which may occur both in men and in women. The term "androgenic alopecia" means hair deficiency states usually caused by a genetically determined hypersensitivity of the hair root to 5α-dihydrotestosterone (DHT).

A typical example of androgenic alopecia is the common baldness in men. However, androgenic alopecia may also occur in women of sexually mature age.

A prerequisite of the treatment of androgenic hair loss is early interruption of the pathogenic processes leading to degeneration of the hair follicle. To achieve normalization of the hair cycle, i.e. a prolongation of the growth phase of the hair, it is necessary to reduce the stimulation of the DHT receptors in the dermal papilla (hair root), i.e. the zone of growth of the hair shaft. Suitable in principle for this purpose are blockade of androgen (DHT) receptors and reduction of the biologically active amount of androgen in the dermal papilla of the follicles. If endocrinopathies are ruled out and medicaments containing testosterone or other substances having androgenic activity are discontinued, it is necessary to inhibit androgen stimulation at the target organ. Accordingly, to achieve this objective, two ways are theoretically conceivable: firstly inhibition of 5α-reductase activity and thus reduction of the conversion of testosterone into 5α-dihydrotestosterone, for example by estrogen or 5α-reductase inhibitor, and secondly blockade of the dihydrotestosterone-sensitive receptor protein, for example by antiandrogens. The second way is expected to be more effective because no accumulation of testosterone, whose activity is weaker than that of DHT but is still pronounced, occurs.

Since all therapeutic procedures for androgenic alopecia are directed against the androgenic effect systemic use thereof is possible for women of childbearing age only with simultaneous contraception. After the introduction of the oral anticontraceptive it emerged that the course of androgenic alopecia and its concomitant symptoms is influenced favorably or unfavorably depending on the product administered, whether higher-estrogen or having a partial antiandrogenic effect or having a residual androgenic effect.

In the absence of another risk-free alternative of greater activity, to date estrogen-containing hair lotions have been prescribed for topical treatment of androgenic alopecia in men. In women, this local therapy is recommended as supporting measure, and the main emphasis is put on systemic treatment with a combination of a progestin having a partial antiandrogenic effect and an estrogen. Male androgenic alopecia can moreover be treated systemically with the 5α-reductase inhibitor finasteride, although with limited success (Van Neste et al., Brit. J. Dermatol. 143, 804–10, 2000; McClellan & Markham, Drugs, 57, 111–26, 1999).

In the case of local therapy, all patients are instructed to treat the region of the scalp on which hair is still present, and not the areas which are already bald. In many cases it is possible by these measures to alleviate or stop the episodes of hair loss. Regeneration of hair follicles which have already atrophied (baldness) is not possible.

Topically active antiandrogens are disclosed in French patent 2 693 461 and U.S. Pat. No. 5,411,981 (4-[3-(4-hydroxybutyl)-4,4-dimethyl-2,5-dioxo-1-imidazolidinyl]-2-(trifluoromethyl) benzonitrile), but are currently not yet generally available for the purposes of therapy.

Both classes of substances show after topical administration a high binding affinity for the androgen receptor of the hair root and a virtual absence of systemic activity.

Because of the teratogenicity, intrinsic to these substances, of antiandrogens having an influence on sex differentiation in the late stage of pregnancy, said substances cannot be used in the form of conventional hydroalcoholic hair lotions because precipitates of the substance occur at the application site after evaporation of the solvent, which is associated with the toxicological risk of transfer of the substance to pregnant women. In addition, delayed release of active ingredient over a prolonged period to avoid high systemic concentrations of active ingredient, and the occurrence, associated therewith, of systemic antiandrogenic effects, is not ensured by conventional preparations for application to the scalp.

In order to be able to provide antiandrogenic active ingredients for safe and effective therapy in the abovementioned patents, it was therefore necessary to find formulations which do not have the described disadvantages of conventional compositions for treating the scalp.

The object is solved by the preparations of the invention comprising one or more antiandrogenic derivatives of the formula I and lipid nanoparticles or a nanoemulsion. The preparation of the invention is advantageous because the lipid nanoparticles and the nanoemulsion preferentially migrate to the hair follicles, and the antiandrogenic derivatives of the formula I are sufficiently firmly connected to the lipids (solution, stable adsorption) and are then cleaved in the hair follicle, by esterases, to give the active antiandrogens. In addition, the preparations of the invention prevent the unwanted precipitation of the antiandrogens at the application site. A contamination of third parties is precluded also by the good miscibility of the carrier lipids and of the epidermal lipids. The very close connection with the endogenous skin lipids markedly exceeds the conventional topical agents (cream, ointment).

The invention, therefore, relates to a pharmaceutical preparation comprising at least one type of lipid nanoparticles and at least one compound of the formula I

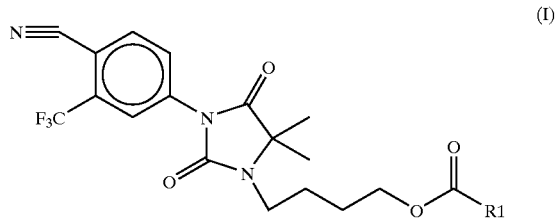

and/or one stereoisomeric form of the compound of the formula I and/or one physiologically tolerated salt of the compound of the formula I, in which R1 is —($C_5$–$C_{17}$)-alkyl or —($C_5$–$C_{17}$)-alkenyl.

A further aspect of the invention relates to a pharmaceutical preparation comprising compounds of the formula I, in which R1 is —($C_{11}$–$C_{15}$)-alkyl or —($C_{11}$–$C_{15}$)-alkenyl.

A further aspect of the invention relates to a pharmaceutical preparation comprising the compound of the formula II

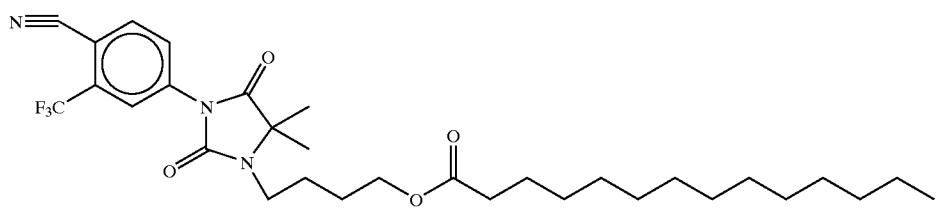

(II)

The preparations of the invention are distinguished primarily by the ability to accumulate the active ingredient in the hair follicle. Further advantages of the preparation of the invention which should be mentioned are good adhesion to the skin and protection of the active ingredient from degradation processes in the drug form.

This ensures that therapeutically effective antiandrogen concentrations are reached at the target organ—the hair root—over a prolonged period without transiently high concentrations occurring in the blood, which by their nature lead to systemic stress for the patient.

A further aspect of the invention relates to novel compounds of the formula I

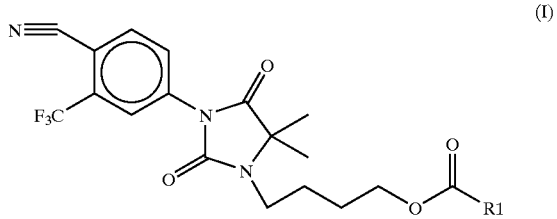

(I)

and/or a stereoisomeric form of the compound of the formula I and/or a physiologically tolerated salt of the compound of the formula I, in which R1 is —($C_5$–$C_{17}$)-alkyl or —($C_5$–$C_{17}$)-alkenyl.

A further aspect of the invention relates to a compound of the formula I, in which R1 is —($C_{11}$–$C_{15}$)-alkyl or —($C_{11}$–$C_{15}$)-alkenyl.

A further aspect of the invention relates to the compound of the formula II

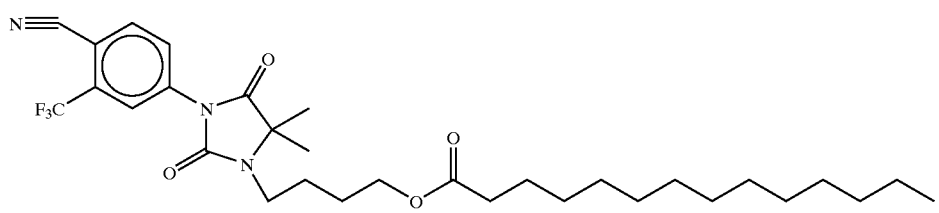

(II)

The term "—($C_5$–$C_{17}$)-alkyl" means hydrocarbon radicals whose carbon chain is straight-chain or branched and comprises from 5 to 17 carbon atoms, for example pentyl, isopentyl, neopentyl, hexyl, 2,3-dimethylbutyl, neohexyl, heptyl, octanyl, nonanyl, decanyl, dodecanyl, pentadecanyl or heptadecanyl.

The term "($C_5$–$C_{17}$)-alkenyl" means hydrocarbon radicals like the abovementioned ($C_5$–$C_{17}$)-alkyl radicals whose carbon chain is straight-chain or branched and comprises from 5 to 17 carbon atoms, and which additionally comprise 1, 2 or 3 double bonds, depending on the chain length.

The antiandrogens are known and can be prepared by processes known from the literature (U.S. Pat. No. 5,411,981).

A further aspect of the invention relates to a process for preparing the compound of the formula I and/or of a stereoisomeric form of the compound of the formula I and/or of a physiologically tolerated salt of the compound of the formula I, which comprises a) reacting a compound of the formula III

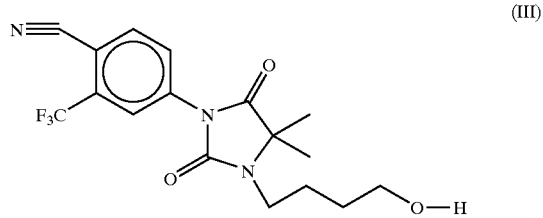

(III)

with an activated fatty acid of the formula IV

(IV)

in which R1 is as defined in formula I, and X is a halogen radical, to give a compound of the formula I, or b) fractionating a compound of the formula I which has been prepared by process a) and which, because of its chemical structure, occurs in enantiomeric forms, by salt formation with enantiopure acids or bases, chromatography on chiral stationary phases or derivatization using chiral compounds such as amino acids, separation of the diastereomers obtained in this way, and elimination of the chiral groups, into the pure enantiomers, or c) either isolating the compound of the formula I which has been prepared by process a) in free form or, in the cases where acidic or basic groups are present, converting it into physiologically tolerated salts.

The reactions take place for example by reacting an acid chloride with the alcoholic hydroxyl group in the presence of a base, for example triethylamine, and of an organic solvent, for example chloroform. The reaction product is purified by chromatography.

In step b) of the process, the compound of the formula I is, if it occurs in diastereoisomeric or enantiomeric form and results as mixtures thereof in the chosen synthesis, separated into the pure stereoisomers, either by chromatography on an optionally chiral support material or, if the racemic compounds of the formula I are able to form salts, by fractional crystallization of the diastereomeric salts formed with an optically active base or acid as auxiliary. Examples of suitable chiral stationary phases for thin-layer or column chromatographic separation of enantiomers are modified silica gel supports (called Pirkle phases) and high molecular weight carbohydrates such as triacetylcellulose. Gas chromatographic methods on chiral stationary phases can also be used for analytical purposes after appropriate derivatization known to the skilled worker. To separate enantiomers of the racemic carboxylic acids, diastereomeric salts differing in solubility are formed using an optically active, usually commercially available, base such as (−)-nicotine, (+)- and (−)-phenylethylamine, quinine bases, L-lysine or L- and D-arginine. The less soluble component is isolated as solid, the more soluble diastereomer is deposited from the mother liquor, and the pure enantiomers are obtained from the diastereomeric salts obtained in this way. It is possible in the same way in principle to convert the racemic compounds of the formula I containing a basic group such as an amino group with optically active acids such as (+)-camphor-10-sulfonic acid, D- and L-tartaric acid, D- and L-lactic acid and (+) and (−)-mandelic acid into the pure enantiomers. Chiral compounds containing alcohol or amine functions can also be converted with appropriately activated or, where appropriate, N-protected enantiopure amino acids into the corresponding esters or amides, or conversely chiral carboxylic acids can be converted with carboxyl-protected enantiopure amino acids into the amides or with enantiopure hydroxy carboxylic acids such as lactic acid into the corresponding chiral esters. The chirality of the amino acid or alcohol residue introduced in enantiopure form can then be utilized for separating the isomers by carrying out a separation of the diastereomers which are now present by crystallization or chromatography on suitable stationary phases, and then eliminating the included chiral moiety by suitable methods.

Acidic or basic products of the compound of the formula I can exist in the form of their salts or in free form. Preference is given to pharmacologically suitable salts, e.g., alkali metal or alkaline earth metal salts, and hydrochlorides, hydrobromides, sulfates, hemisulfates, all possible phosphates, and salts of amino acids, natural bases or carboxylic acids.

Physiologically tolerated salts are prepared from compounds of the formula I able to form salts, including their stereo isomeric forms, as in step c) of the process in a manner known per se. The compounds of the formula I form with basic reagents such as hydroxides, carbonates, bicarbonates, alcoholates and ammonia or organic bases, for example trimethyl- or triethylamine, ethanolamine or triethanolamine or else basic amino acids, for example lysine, ornithine or arginine, stable alkali metal, alkaline earth metal or optionally substituted ammonium salts. Where the compounds of the formula I have basic groups, stable acid addition salts can also be prepared with strong acids. Suitable for this purpose are both inorganic and organic acids, such as hydrochloric, hydrobromic, sulfuric, phosphoric, methanesulfonic, benzenesulfonic or p-toluenesulfonic, 4-bromobenzenesulfonic, cyclohexylsulfamic, trifluoromethylsulfonic, acetic, oxalic, tartaric, succinic or trifluoroacetic acid.

The invention also relates to medicaments having an effective content of at least one compound of the formula I and/or one physiologically tolerated salt of the compound of the formula I and/or an optionally stereoisomeric form of the compound of the formula I, together with a pharmaceutically suitable and physiologically tolerated carrier, additive and/or other active ingredients and excipients.

A further aspect of the invention relates to a process for producing the preparation of the invention, which comprises high-pressure homogenization of the compound of the formula I in a hot lipid/surfactant solution, inclusion of the compound of the formula I taking place, and subsequent cooling. The cooling results in a dispersion of solid lipid particles comprising the compound of the formula I. The size of the lipid particles is less than 1 μm.

A further aspect of the invention relates to a process for producing the preparation of the invention, which comprises high-pressure homogenization of the compound of the formula I with lipids which are liquid at room temperature. By room temperature is meant in this connection temperatures from 18° C. to 25° C. Lipids which can be employed are, for example, Miglyol® lipid, identified as a medium chain, caprylic/capric triglyceride. This production process leads to so-called nanoemulsions which differ from the solid lipid nanoparticles through the use of lipids which are liquid at room temperature (e.g., Miglyol) in place of solid ones.

In general, the preparations of the invention are produced in a manner known per se by incorporating the compounds of the formula I into the particles by high-pressure homogenization.

For this purpose, a surfactant (e.g., poloxamer 188) and water, and the compound of the formula I and the lipid, are weighed for example into two vessels. Both vessels are heated in a water bath to the temperature at which the hot homogenization is to take place. This temperature is usually at least 10° C. above the melting point of the lipid. The lipid liquefies during this. The compound of the formula I is dissolved in the melt of the lipid. After the solutions have approximately reached the temperature of the water bath, the surfactant solution is added to the lipid solution of the compound of the formula I. This mixture is preemulsified with a rotor-stator mixer (for example Ultra-Turrax) and then homogenized using a high-pressure homogenizer (e.g., EmulsiFex-B3, Avestin; LAB 40, APV-Gaulin) (e.g., 3 cycles at 500 bar). After the production process, the lipid nanodispersion obtained is cooled in a water bath at, for example, 22° C., whereupon the lipid crystallizes out to form lipid nanoparticles.

The lipid nanoparticles consist of a solid lipid phase which is dispersed in an emulsifier-containing aqueous phase. Physiologically well-tolerated lipids are employed as lipid phase, for example glyceryl behenate or glyceryl palmitostearate and/or phosphatidylethanolamine, with which the compound of the formula I is in associated form after the lipid particles have formed. Addition of the surfactant serves to stabilize the lipid nanoparticle dispersion. The average particle diameter of lipid nanoparticles is in the range from 50 nm to 1 000 nm, frequently in the range from 200 nm to 400 nm.

The preparations of the invention are primarily distinguished by targeted transport of the compound of the formula I into the hair follicle and by slowed release of the compound of the formula I.

The pharmaceutical preparations are preferably liquid preparations such as hair lotions or hair tonics, which may comprise as main ingredients water and lipids (e.g., Precirol (glycerine palmito-stearate), Compritol® (behenate composition), Monosteol (propylene glycol palmito stearate), Imwitor® (glyceryl monostearate), Softisan® (hydrogenated palm oil), phosphatidylethanolamine), and surfactants (e.g., poloxamer), but also aqueous ($C_1$–$C_6$)-alcohols such as, for example, ethanol, propanol, butanol, pentanol, hexanol or isopropanol, also lotions or semisolid preparations such as emulsions, creams, gels or ointments. The preparations may, where appropriate, also be in aerosol form.

Additives which may be present in the preparations of the invention are also at least one compound which promotes blood flow, such as dihydralazine, diisopropylamine, aminexil, diazoxide or calcium channel blockers such as nifedipine, nicardipine, verapamil, diltiazem, nisoldipine, nitrendipine, nivaldipine, isradipine, felodipine, nimodipine, gallopamil, fendiline, flunarizine, amlodipine, diperdipine, fluspirilene, primozide, fantofarone, nicergoline or cyclandelate, 6-amino-4-piperidino-1,2-dihydro-1-hydroxy-2-iminopyrimidine (minoxidil), angiotensin-converting enzyme inhibitors such as quinapril, lisinopril, benzapril, captopril, ramipril, fosinopril, cifazapril or trandolapril, methylxanthine compounds such as pentoxifylline, propentofylline, torbafylline or mixtures thereof.

Suitable additives are also at least one sodium channel opener such as 1-cyano-2-(1,1-dimethylpropyl)-3-(3-pyridyl)guanidine or 5-alpha-reductase inhibitors such as N-tertiary-butyl-3-oxo-4-aza-5α-androst-1-ene-17β-carboxamide. Further suitable additives are also at least one compound which promotes hair growth, such as an inner salt of 2,4-diamino-6-alkoxy-3-sulfoxypyrimidine hydroxide with 1 to 6 carbon atoms in the alkoxy radical as described in EP 0 427 625; e.g., the inner salt of 2,4-diamino-6-butoxy-3-sulfoxypyrimidine hydroxide, or pyridine 1-oxide derivatives as described in WO 92/21317; e.g., 2,6-diamino-4-piperidinopyridine, or 2,6-diamino-1,3,5-triazine derivatives as described in WO 91/19701; e.g., 2,6-diamino-4-butoxy-1,3,5-triazine 1-oxide. Mixtures of said additives are also suitable.

Further additives which the preparations of the invention may contain are the hair- and scalp-care substances and medical active ingredients customary in cosmetics, such as, for example, antidandruff agents, products having an antiseborrheic effect, substances having a keratolytic and keratoplastic effect such as salicylic acid, allantoin, sulfur products, urea, ceramides, antimicrobials, vitamins, plant extracts or organ extracts, hormones, corticoids, hyperemic agents such as nicotinic acid and derivatives thereof, organic acids such as citric acid, orotic acid, lipoic acid, amino acids, polyethoxylated fatty alcohols, fatty acids, sorbitan fatty acid esters, alkyl phosphates and oils, e.g., fatty acid esters, and in addition preservatives, colors and perfume oils. It is essential that the additives are compatible with antiandrogenic substances and do not inhibit the hair-growth effect thereof. They must moreover not promote systemic uptake of the antiandrogen.

The preparations of the invention can be used to treat androgenic alopecia in a safe and effective manner. This is an extremely important finding in the light of the poor results of therapy to date.

The preparations of the invention are also suitable for the treatment of hirsutism, that is to say, to prevent unwanted hair growth. The preparations are also suitable to treat seborrhea and acne.

The amount of the active ingredient in the preparations of the invention is generally from 0.01% by weight to 10% by weight, preferably 0.1 to 5% by weight.

The invention further relates to the use of the preparations of the invention in cosmetics. The cosmetic compositions are presented in the form of a cream, milk, lotion, gel, microspheres or nanospheres or lipid or polymeric vesicles, soaps or shampoos. In one embodiment, the concentration of the compound of the formula I in the cosmetic composition ranges from 0.001% to 3% by weight relative to the total weight of the composition. Thus, the invention provides a cosmetic composition of matter comprising a cosmetically effective amount of a compound according to formula I, or a cosmetically acceptable salt thereof, and a cosmetically acceptable vehicle, carrier or diluent therefor.

EXAMPLE 1

Preparation of the Compound of the Formula II:

300 mg of 4-[3-(4-hydroxybutyl)-4,4-dimethyl-2,5-dioxo-1-imidazolidinyl]-2-(trifluoro-methyl)benzonitrile, compound 1 hereinafter, ($8.13 \times 10^{-4}$ mol) were reacted with 400 mg of myristoyl chloride ($1.62 \times 10^{-3}$ mol) in the presence of 0.5 ml of triethylamine in 10 ml of absolute chloroform with stirring for 24 hours (h). After completion of the reaction, the formation of a lipophilic product was observed by a TLC check (silica gel plate, eluant ethyl acetate). A Chromatotron was used (methylene chloride as eluant) for quantitative removal of the presumed ester. The organic solution of the removed reaction product was evaporated, recrystallized with water from methanol/chloroform and dried. The compound of the formula II was identified on the basis of $^{1}$H NMR (400 MHz) spectroscopy, mass spectroscopy and C—H—N analysis, and $^{13}$C NMR, and H—H and C—H Cosy spectra:

$^{1}$H—NMR (CDCl$_3$; 400,132 MHz, ppm): 0.88 (m, 3H, CH$_3$); 1.25 (m, 20H, CH$_2$); 1.54 (s, 6H, CH$_3$); 1.69–1.81 (m, 6H, CH$_2$); 2.30 (m, 2H, CH$_2$); 3.39 (m, 2H, CH$_2$); 4.13 (m, 2H, CH$_2$); 7.91 (d, 1H, ar); 8.01 (d, 1H, ar); 8.16 (s, 1H, ar).

$^{13}$C—NMR (CDCl$_3$; 100,625 MHz): distinct signals at ppm: 14.12; 22.69; 23.51; 25.0; 26.15; 26.30; 29.18; 29.28; 29.36; 29.48; 29.61; 29.65; 29.68; 31.93; 34.32; 40.0; 61.87; 63.34; 1208.25; 115.02; 122.89; 122.94; 122.97; 123.04; 123.35; 127.85; 135.27; 136.50; 152.85; 173.67; 174.56.

The melting point of the compound of the formula II is 70.7° C. to 72.4° C.

The yield was 260 mg ($4.49 \times 10^{-4}$ mol). This corresponds to a yield of 55.2%.

Mass spectrum MS: 579.7

Molecular composition:

C 64.23%; H 7.65%; F 9.83%; N 7.25%; O 11.04%

CHN analysis:

| Atom | Theoret. value | 1st Measurement | 2nd Measurement |
|------|----------------|-----------------|-----------------|
| C | 64.23 | 63.97 | 63.86 |
| H | 7.651 | 7.706 | 7.945 |
| N | 7.249 | 6.942 | 7.029 |

EXAMPLE 2

The preparation of the invention has, for example, the following composition (% by weight):

| Compound of the formula II | 0.1–1% |
|---|---|
| a) | |
| Compritol | 5% |
| Poloxamer | 1.25% |
| b) | |
| Precirol | 5% |
| Poloxamer | 1.25% |
| c) | |
| Monosteol | 5% |
| Poloxamer | 1.25% |

EXAMPLE 3

Production of the Preparation:

0.05 g of poloxamer 188 and 3.746 ml of water, and 0.004 g of the compound of example 1, compound 2 hereinafter, and 0.2 g of the lipid (for example Precirol), were weighed into two vessels. Both vessels were heated to a temperature of 80° C. in a water bath. The lipid liquefied during this. Compound 2 was dissolved in the melt of the lipid. After the solutions had approximately reached the temperature of the water bath, the surfactant solution was added to the lipid solution or lipid dispersion of the compound of the formula I. This mixture was pre-emulsified with a rotor-stator mixer (Ultra-Turrax) at 8 000 rpm for 10 sec and then homogenized using a high-pressure homogenizer (EmulsiFlex-B3, Avestin) with 3 cycles at 500 bar. After the production process, the lipid nanodispersion obtained was cooled in the water bath to a temperature of 22° C., whereupon the lipid crystallized out to form lipid nanoparticles. The yield of crystalline lipid was 98.3%.

The produced nanoparticles and the nanoemulsion had the following physical characteristics:

TABLE 1

| | | Laser diffractometry (LD) | | | | | |
|---|---|---|---|---|---|---|---|
| | | Day 3 (4) | | Day 16 | | Day 44 | |
| Lipid | | LD 50% ($\mu$m) | LD 95% ($\mu$m) | LD 50% ($\mu$m) | LD 95% ($\mu$m) | LD 50% ($\mu$m) | LD 95% ($\mu$m) |
| Compritol | with compound 2 | 0.214 | 0.563 | 0.211 | 0.640 | n. d. | n. d. |
| | without compound 2 | 0.249 | 0.586 | 0.260 | 0.615 | n. d. | n. d. |
| Precirol | with compound 2 | 0.199 | 1.963 | 0.181 | 1.544 | 0.108 | 0.295 |
| | without compound 2 | 0.151 | 0.843 | 0.185 | 1.877 | 0.089 | 0.249 |
| Monosteol | with compound 2 | 36.62 | 74.01 | 20.72 | 46.25 | n. d. | n. d. |
| | without compound 2 | 19.47 | 112.5 | 16.65 | 51.01 | n. d. | n. d. |
| Nanoemulsion (Miglyol) | | 0.171 | 0.920 | 0.149 | 0.149 | n. d. | n. d. |

LD 50% (LD 95%): 50% (or 95%) of the particles are smaller than the stated diameter (according to: Mehnert & Mäder, Adv. Drug Delivery Rev. 47, 165–196, 2001)

TABLE 2

| | Photon correlation spectroscopy (PCS) | | | |
|---|---|---|---|---|
| | | Average diameter ($\mu$m) | | |
| Lipid | SLN | Day 3 (4) | Day 16 | Day 44 |
| Compritol | with compound 2 | 0.255 | 0.214 | n.d. |
| | without compound 2 | 0.259 | n.d. | n.d. |
| Precirol | with compound 2 | 0.214 | n.d. | 0.211 |
| | without compound 2 | 0.224 | n.d. | n.d. |
| Monosteol | with compound 2 | 0.266 | n.d. | n.d. |
| | without compound 2 | 0.261 | n.d. | n.d. | n.d. means not determined (according to: Mehnert & Mäder, Adv. Drug Delivery Rev. 47, 165–196, 2001)

The results show that the particle size remains stable on storage. In addition, incorporation of the active ingredient does not have an adverse effect on the stability of the preparation. In addition, distinct melting peaks in the differential calorimetry investigation prove that solid particles are present. Microscopic investigations revealed no indications of crystallization of compound 2.

EXAMPLE 4

Investigations of the receptor affinity of compounds 1 and 2 took place with 29+/GR+ cells which express the androgen receptor (List et al.; Exp. Cell Res. 250; 414–422; 1999). The affinity was determined by comparison with dihydrotestosterone (DHT). The $EC_{50}$ values obtained were DHT 0.27 nM; compound 1 6.7 nM and compound 2 11 045 nM. It is probable that the binding of compound 2 is not derived from the ester function but from enzymatic or spontaneous hydrolysis of the ester. Compound 2 is accordingly a prodrug of compound 1.

Release of the active compound 1 from the lipid particles in which they are present as compound 2 was proved by investigations on skin cell cultures. Monolayer cultures of juvenile prepuce keratinocytes and fibroblasts and of cells of the dermal papilla of occipital scalp were incubated with compound 2 in a concentration of $10^{-5}$ M under standard conditions (5% $CO_2$, 37° C.) for 24 h. The cell culture medium was then extracted with chloroform. The organic phase was evaporated and the residue was taken up in acetonitrile and investigated by HPLC analysis for its content of compounds 1 and 2.

TABLE 3

Hydrolysis of compound 2 in cultivated human skin cells (DP, dermal papilla; FB, fibroblasts; KC, keratinocytes). The cells were cultivated with compound 2 under standard conditions (5% $CO_2$, 37° C.) for 24 h. Extracts of the media were analyzed by HPLC (n = 3).

| Strain | Compound 1 formation | |
| --- | --- | --- |
| | pmol/μg protein | % per mixture |
| DP 03/99 | 177.9 ± 23.4 | 49.6 ± 6.5 |
| FB x2712 | 166.7 ± 24.7 | 34.2 ± 5.1 |
| FB x1412 | 158.9 ± 17.0 | 56.1 ± 6.0 |
| FB x1 | 81.4 ± 12.7 | 57.0 ± 8.9 |
| KC x608 | 21.6 ± 0.8 | 21.6 ± 0.8 |
| KC x709 | 20.3 ± 1.3 | 25.4 ± 1.7 |

It follows from this that significant conversion of compound 2 into compound 1 occurs in skin cells. This also applied in particular to cells of the dermal papilla, which represent the target for antiandrogens like compound 1.

What is claimed is:

1. A compound of the formula I

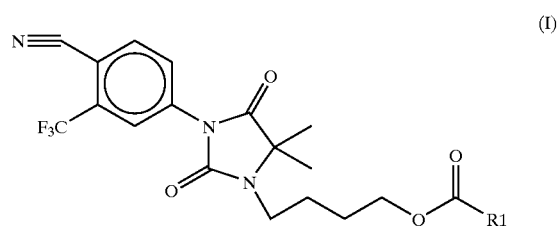

or a stereoisomeric form of the compound of the formula I or a physiologically tolerated salt of the compound of the formula I, in which R1 is —($C_{11}$–$C_{15}$)-alkyl or —($C_{11}$–$C_{15}$)-alkenyl.

2. A compound of the formula I as claimed in claim 1, which is the compound of the formula II

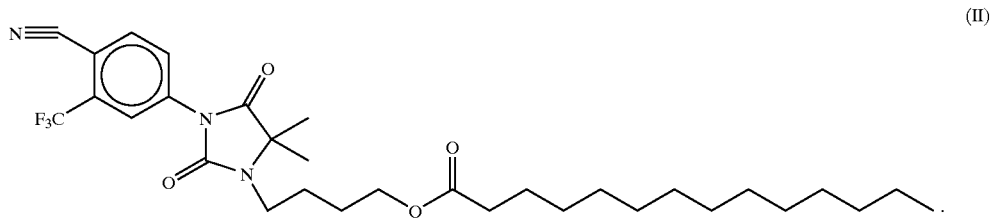

3. A pharmaceutical preparation comprising at least one lipid nanoparticle and at least one compound of the formula I as claimed in claim 1

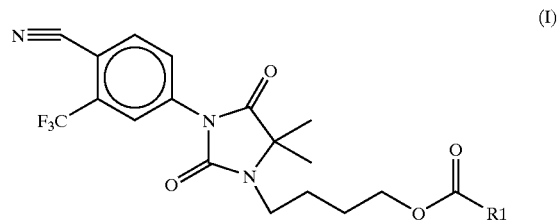

or one stereoisomeric form of the compound of the formula I or one physiologically tolerated salt of the compound of the formula I, in which R1 is —($C_{11}$–$C_{15}$)-alkyl or —($C_{11}$–$C_{15}$)-alkenyl.

4. A pharmaceutical preparation as claimed in claim 3, which comprises a compound of the formula II

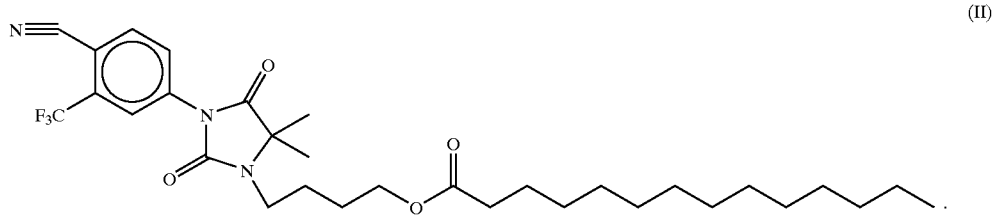

(II)

5. A process for preparing the compound of the formula I as claimed in claim 1, which comprises
a) reacting a compound of the formula III

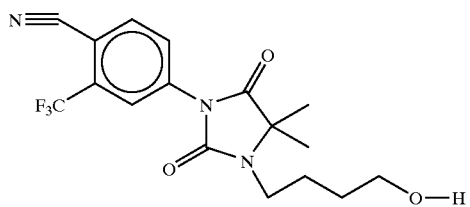

(III)

with an activated fatty acid of the formula IV

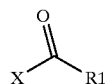

(IV)

in which R1 is as defined in claim 1, and X is a halogen radical, to give a compound of formula I as claimed in claim 1, or
b) fractionating a compound of formula I which has been prepared by process a) and which, because of its chemical structure, occurs in enantiomeric forms, by salt formation with enantiopure acids or bases, chromatography on chiral stationary phases or derivatization using chiral compounds, separation of the diastereomers obtained in this way, and elimination of the chiral groups, into the pure enantiomers, or
c) either isolating the compound of formula I as claimed in claim 1 which has been prepared by process a) in free form or, in the cases where acidic or basic groups are present, converting it into physiologically tolerated salts.

6. A medicament having an effective content of at least one compound of formula I as claimed in claim 1 together with a pharmaceutically suitable and physiologically tolerated carrier, additive, other active ingredients and excipients, or combinations thereof.

7. A process for producing the pharmaceutical preparation as claimed in claim 3, which comprises high-pressure homogenization of the compound of formula I in a hot lipid/surfactant solution and subsequent cooling.

8. A process for producing the preparation as claimed in claim 3, which comprises high-pressure homogenization of the compound of formula I with lipids which are liquid at room temperature.

9. The process for producing the preparation as claimed in claim 8, wherein a surfactant and water are weighed into one vessel, and the compound of formula I and a lipid are weighed into another vessel, the contents of the two vessels are heated to a temperature which is about 10° C. above the melting point of said lipid, and then the contents of the two vessels are combined and the mixture is homogenized using a high-pressure homogenizer and finally cooled, whereupon the lipid crystallizes out to form lipid nanoparticles.

10. The process as claimed in claim 7, wherein Precirol, Compritol, Monosteol, Imwitor, Softisan, phosphatidylethanolamine or a mixture of these lipids is employed as lipid, and poloxamer is employed as surfactant.

11. A method for the treatment of androgenic alopecia, hirsutism, seborrhea or acne comprising the administration of a pharmaceutically effective amount of a medicament comprising a compound as claimed in claim 1.

12. A cosmetic composition of matter comprising a cosmetically effective amount of a compound as claimed in claim 1, or a cosmetically acceptable salt thereof, and a cosmetically acceptable vehicle, carrier or diluent therefor.

* * * * *